United States Patent
Duffy et al.

(10) Patent No.: US 7,091,286 B2
(45) Date of Patent: *Aug. 15, 2006

(54) LOW-CURE POWDER COATINGS AND METHODS FOR USING THE SAME

(75) Inventors: Shawn P. Duffy, Cheswick, PA (US); Anthony M. Chasser, Allison Park, PA (US); Ronald R. Ambrose, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 361 days.

This patent is subject to a terminal disclaimer.

(21) Appl. No.: 10/673,313

(22) Filed: Sep. 29, 2003

(65) Prior Publication Data

US 2004/0067367 A1    Apr. 8, 2004

Related U.S. Application Data

(63) Continuation-in-part of application No. 10/160,466, filed on May 31, 2002, now Pat. No. 6,737,163.

(51) Int. Cl.
| | |
|---|---|
| *C08G 18/28* | (2006.01) |
| *C08L 63/00* | (2006.01) |
| *C08L 63/02* | (2006.01) |
| *C08L 83/05* | (2006.01) |

(52) U.S. Cl. .............. 525/454; 428/413; 428/416; 428/447; 428/457; 428/458; 428/480; 428/483; 428/500; 428/511; 525/100; 525/101; 525/123; 525/125; 525/131; 525/166; 525/176; 525/187; 525/453; 525/486; 525/502; 525/504; 525/528; 528/68; 528/85

(58) Field of Classification Search ............ None
See application file for complete search history.

(56) References Cited

U.S. PATENT DOCUMENTS

| 4,324,739 A | 4/1982 | Zondler et al. ........ 260/465.4 |
| 4,562,241 A | 12/1985 | Renner ................. 528/99 |
| 5,470,886 A * | 11/1995 | Makhlouf et al. ......... 521/59 |
| 5,569,733 A | 10/1996 | Donnelly et al. ......... 528/61 |
| 5,714,206 A | 2/1998 | Daly et al. .............. 427/475 |
| 5,907,020 A | 5/1999 | Correll et al. ........... 525/526 |
| 6,077,610 A | 6/2000 | Correll et al. ........... 428/413 |
| 6,335,003 B1 * | 1/2002 | Kim et al. ............. 424/70.17 |
| 6,737,163 B1 * | 5/2004 | Chasser et al. ........... 428/418 |
| 6,759,363 B1 * | 7/2004 | Haas et al. ............. 502/167 |

FOREIGN PATENT DOCUMENTS

| DE | 19512479 | 10/1996 |
| EP | 0594133 | 4/1994 |
| WO | WO 03/10244 | 12/2003 |

* cited by examiner

*Primary Examiner*—Robert Sellers
(74) *Attorney, Agent, or Firm*—Diane R. Meyers; Donald R. Palladino

(57) ABSTRACT

Low-cure powder coating compositions are disclosed, comprising at least one epoxy-containing resin and/or at least one siloxane-containing resin, and at least one material having the structure

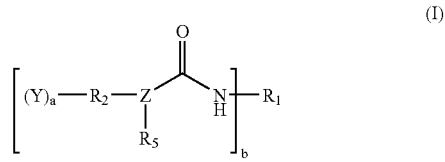

wherein $R_1$ is an organic radical having 6 to 25 carbon atoms; each $R_2$ is independently a multivalent hydrocarbon group having 1 to 20 carbon atoms; Y is

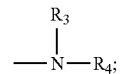

each $R_3$ and $R_4$ are independently alkyl or aryl groups having 1 to 8 carbon atoms; each Z is independently oxygen or nitrogen; $R_5$ is absent when Z is oxygen and $R_5$ is hydrogen, an alkyl or aryl group having 1 to 20 carbon atoms, or $(Y)_a$—$R_2$— when Z is nitrogen; a and b are integers; a is at least 1; b is 1 to 3; and (b) at least one epoxy-containing resin and/or at least one siloxane-containing resin. The material can optionally be reacted with an acidic hydrogen-containing compound. Some compositions are curable without using crosslinking agents or accelerators. Methods for coating a substrate using these compositions, the coated substrates, and additional catalysts useful for the same purpose are also disclosed.

16 Claims, No Drawings

LOW-CURE POWDER COATINGS AND METHODS FOR USING THE SAME

CROSS REFERENCE TO RELATED APPLICATIONS

This application is a continuation-in-part of Ser. No. 10/160,466, filed May 31, 2002, now U.S. Pat. No.6,737, 163, the contents of which are incorporated by reference herein.

FIELD OF THE INVENTION

The present invention relates to powder coating compositions; more particularly, the present invention relates to low temperature cure thermosetting powder coating compositions. The compositions consistently produce coatings that have desirable performance properties when cured, and that are stable when uncured.

BACKGROUND OF THE INVENTION

Coating compositions have long been used to provide the surface of articles with certain desired physical characteristics, such as color, gloss and durability. Many coating compositions rely on a liquid carrier, which evaporates after the composition is applied. In recent years, powder coatings have become increasingly popular; because these coatings are inherently low in volatile organic content (VOCs), their use reduces air emissions during the application and curing processes as compared with liquid coatings.

Powder coatings are typically cured by heating the coated substrate to an elevated temperature. These temperatures almost always exceed 125° C., and commonly reach about 190° C. to 205° C. During the curing process, the powder particles melt, flow, and coalesce, and the components of the powder coating react. In addition to not emitting any VOCs into the environment during the application or curing processes, powder coating systems are extremely efficient since there is essentially no waste (i.e., application yield is approximately 100 percent). Because of the relatively high (i.e., greater than 125° C.) cure temperatures of most powder coatings, their use, for practical purposes, is often limited to substrates that can withstand such high temperatures or that can be heated to an appropriate temperature long enough for cure to occur.

Despite the desirability of low-cure powder compositions, two problems have prevented their widespread production and use—their mechanical stability and their chemical stability. Conventional powders that use resins with a glass transition temperature ("Tg") lower than 60° C. may encounter package stability problems, especially after prolonged heat exposure, and become fused, sintered or clumpy within days. Similarly, prolonged heat exposure can destroy the chemical stability of a powder if it includes crosslinkers that react at temperatures below about 170° C.; if a crosslinker with a lower cure temperature is used, cure may be initiated during storage even though the film has not been formed. The premature gelation that occurs in these powder formulations results in coatings having shortened gel times. It is not unusual for low-cure powders to lose >50 percent of their gel time as a result of the premature gelation.

Problems encountered when a powder loses either mechanical or chemical stability can be severe. Poor mechanical stability creates obvious handling, application and appearance issues. Poor chemical stability creates subtler yet just as problematic issues. For example, a powder that has poor chemical stability will fluidize and apply like virgin powder, but because it has advanced in reactivity (i.e. undergone some premature gelation), it demonstrates restricted flow or no flow at all during cure. The result can be a coating having an "orange peel" appearance, a rough texture or gel bodies.

Ideally, a powder should not lose its handling properties under elevated temperature storage and the gel time should remain the same as that of the virgin material. To achieve this, powders are typically formulated with resins having a Tg greater than about 60° C. and/or crosslinkers that react at temperatures of about 170° C. or greater. Such powders, however, are not low cure. Low-cure powders having lower Tg resins or lower temperature crosslinkers can require expensive storage under refrigeration and air-conditioned application facilities to overcome their inherent lack of stability, or must be prepared using special techniques.

Thus, there is a need in the coatings art for low-cure powder coatings having a wide range of application, which also have an acceptable level of durability when cured on the finished product and good stability at room temperature.

SUMMARY OF THE INVENTION

The present invention is directed to curable powder coating compositions generally comprising (a) at least one tertiary aminourea compound, at least one tertiary aminourethane compound, or mixtures thereof, and (b) at least one film-forming epoxy-containing resin and/or at least one siloxane-containing resin. It has been surprisingly discovered that these resins, when used with the present tertiary aminourea and/or aminourethane compounds, cure to form a suitable coating without the aid of crosslinkers, accelerators, or other additives typically regarded in the art as being necessary to cure these resins. The cured coatings that result from the present compositions have performance properties that are at least as good as powder coating compositions prepared with the same resins and conventional curing agents, but lacking the tertiary aminourea or aminourethane compositions described herein. Significantly, this desirable result is achieved by using curing temperatures much lower than those used for conventional products. Accordingly, the present compositions are low-cure. "Low-cure" as used herein refers to powder coating compositions that cure at a temperature between about 80° C. and 125° C. However, the present invention is not limited to this temperature range and also provides cured films at temperatures up to and even greater than 190° C.

As a result of being low-cure, the present compositions can be used on substrates that are sensitive to temperatures greater than about 125° C. Examples include, but are not limited to, plastics such as thermoset and thermoplastic compositions, and wood. These compositions may also be used to coat pieces of thick metal that cannot be heated above about 95° C. because of their size. Also suitable are articles of manufacture that include a variety of substrates; for example, motors that contain both metal and rubber components can be suitably coated using the present, low-cure powder compositions.

The present compositions also overcome some of the difficulties that have been observed with other powder coating compositions, particularly other low-cure powders. For example, the present powder compositions are storage stable, and reduce, if not eliminate, the problems with chemical and mechanical stability seen with other low-cure powder compositions. The present compositions can be stored at room temperature, and they do not continue to catalyze the reaction of the resin after the removal of heat. Moreover, the present powder compositions can be prepared using standard methods known in the art for preparing powder coating compositions; no special processing or handling is needed. Thus, the present compositions provide a significant advance in the low-cure powder coatings art.

Methods for coating substrates using the present powder compositions, and substrates coated thereby, are also within the scope of the present invention. Various low-cure catalysts are also included in the present invention.

DETAILED DESCRIPTION OF THE INVENTION

The present invention is directed to a curable powder coating composition comprising: (a) at least one material having the structure of Formula (I):

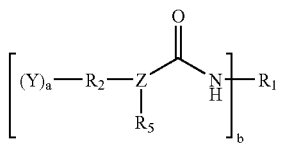

wherein $R_1$ is an organic radical having 6 to 25 carbon atoms; $R_2$ is a multivalent hydrocarbon group having 1 to 20 carbon atoms; Y is

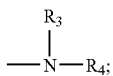

$R_3$ and $R_4$ are independently alkyl or aryl groups having 1 to 8 carbon atoms; Z is oxygen or nitrogen; $R_5$ is absent when Z is oxygen and $R_5$ is hydrogen, an alkyl or aryl group having 1 to 20 carbon atoms, or $(Y)_a$—$R_2$— when Z is nitrogen; a and b are integers; a is at least 1; b is 1 to 3; and (b) at least one epoxy-containing resin and/or at least one siloxane-containing resin. It will be understood that when Z is oxygen, a tertiary aminourethane compound is represented and when Z is nitrogen, Formula I depicts a tertiary aminourea compound. If multiple $R_3$ and $R_4$ groups exist, each $R_3$ and each $R_4$ can be the same or different as any other $R_3$ or $R_4$. For example, one $R_3$ can have one carbon and another have two carbons, and the like. Also, when there are multiple Y, $R_2$ and Z groups, each Y, $R_2$ and Z can be the same or different as other Y, $R_2$ and Z groups. "a", as noted above, is at least 1. Each "a" group can be attached to any of the carbons of the $R_2$ group, even though they are generally depicted in Formula I as being attached to the terminal carbon; more than one "a" group can be attached to a particular carbon. It will be understood that each "b" group will be attached to a carbon from which an isocyanate group extends.

The material of Formula I can be an oligomer wherein $R_1$ is a monovalent, divalent, or trivalent organic radical; divalent radicals are particularly suitable. The $R_1$ radical can be aliphatic, such as hexamethylene, cycloaliphatic such as cyclohexylene, substituted cycloaliphatic such as 1,3,3-trimethylcyclohexylmethylene, or aromatic such as phenylene. Substituted cycloaliphatics are particularly suitable, especially 1,3,3-trimethylcyclohexylmethylene. For example, $R_1$ can be the residue of an isocyanate or polyisocyanate. Examples of suitable $R_2$ moieties include ethylene, n-propylene, and iso- and n-butylene. In a particularly suitable composition, Z is nitrogen, $R_1$ is 1,3,3-trimethylcyclohexylmethylene, $R_2$ is propylene, $R_3$ and $R_4$ are both methyl groups, and $R_5$ is hydrogen.

The material of component (a) can be prepared by reacting an organic polyisocyanate, particularly a diisocyanate, with a polyamine containing a primary or secondary amine group and at least one tertiary amine group for the aminourea embodiment or with an alcohol or polyol containing at least one tertiary amine for the aminourethane embodiment. Suitable polyisocyanates include aliphatic, cycloaliphatic, or aromatic polyisocyanates. Diisocyanates are particularly suitable, although higher polyisocyanates can be used. Examples of suitable aromatic diisocyanates are 4,4'-diphenylmethane diisocyanate, 1,3-bis(1-isocyanato-1-methylethyl)benzene and derivatives thereof, and toluene diisocyanate. Examples of suitable aliphatic diisocyanates are straight chain aliphatic diisocyanates such as 1,6-hexamethylene diisocyanate and cycloaliphatic diisocyanates including isophorone diisocyanate and 4,4'-methylene-bis-(cyclohexyl isocyanate). Examples of suitable higher polyisocyanates are 1,2,4-benzene triisocyanate, polymethylene polyphenyl isocyanate and the isocyanurate of isophorone diisocyanate. Isophorone diisocyanate is especially suitable.

Examples of polyamines containing a primary or secondary amine group and at least one tertiary amine group are dimethylaminopropylamine and 2-amino-5-diethylaminopentane. An example of an alcohol containing a tertiary amine is dimethylaminopropanol. Dimethylaminopropylamine is particularly suitable.

The polyamine or amino alcohol and polyisocyanate are combined in an equivalent ratio of about 1:1. The polyamine is heated to about 50° C., and the polyisocyanate is added over a period of time in the range of about one to two hours, usually about two hours. The amino alcohol typically should be heated to about 80° C. before the polyisocyanate is added. The temperature of the reaction mixture generally increases and is held at an elevated temperature, such as 130° C. to 170° C., until the polyisocyanate is completely reacted.

In one embodiment, the material of component (a) further comprises an acidic hydrogen-containing compound; for example, component (a) can comprise the reaction product of (i) a material having Formula I and (ii) an acidic hydrogen-containing compound. The acidic hydrogen-containing compound of (ii) may be a carboxylic acid, a phenolic compound, a polyester, a polyurethane or an acrylic polymer. Phenolic compounds, especially polyphenols, are particularly suitable. Suitable phenols include phenol itself and polyphenols such as resorcinol, catechol, hydroquinone, bis(4-hydroxyphenyl)-2,2-propane (Bisphenol A), bis(4-hydroxyphenyl)-1,1-isobutane, bis(4-hydroxyphenyl)-1,1-ethane, bis(2-hydroxyphenyl)-methane, 4,4-dihydroxybenzophenone, and 1,5-dihydroxynaphthalene. Bisphenol A is especially suitable.

The reaction product used in the coatings of the present invention can be prepared by mixing the material having Formula I with the acidic hydrogen-containing compound in an equivalent ratio of about 1:1 to 1:2, such as about 1:1.87. The material of Formula I is typically heated to a temperature of about 140° C. to 180° C. and the acidic hydrogen-containing compound is added. The reaction mixture is then usually held at the elevated temperature until it turns clear, indicating homogeneity of the reaction mixture. The reaction mixture is then allowed to cool. Alternatively, the tertiary amine component (polyamine or amino alcohol) is mixed with the acidic hydrogen-containing compound and heated to form a solution. The isocyanate component is then slowly added to form a reaction product, then the product is held at elevated temperature for about thirty minutes and allowed to cool.

Component (a) in the compositions of the present invention, with or without the acidic hydrogen-containing compound, is used as a catalyst, and typically has a melting point of about 23° C. to 150° C., such as about 50° C. to 100° C. This range of melting points helps prevent any curing from taking place in the composition before the application of heat. This improves the long-term stability of curable compositions in which component (a) is used. The melting point of the catalyst is typically not so high, however, that the present compositions lose their characterization as "low-cure". It is, therefore, desirable that the catalyst used in the present compositions have a melting point of about 23° C. to 150° C. If the melting point is too far above this range, the composition might not cure in the desired manner, and at temperatures too much below this range, the composition may not be as stable due to premature crosslinking.

Component (b) in the present compositions is an epoxy-containing resin and/or a siloxane-containing resin. The term "epoxy-containing resin" is used herein to refer to any resin that has epoxy functional groups including, for example, polyepoxide resins and epoxy/hydroxy-containing resins. Similarly, the term "siloxane-containing resin" is used herein to refer to any resin that has siloxane and hydroxyl functionality.

In one embodiment of the present invention, the resin utilized is at least one epoxy/hydroxy-containing resin. As used herein, the term "epoxy/hydroxy-containing resin" refers generally to a composition that comprises both epoxy and hydroxy functionality. Such a resin can be obtained, for example, by mixing one or more epoxy-containing resins and one or more hydroxy-containing resins. Alternatively, one or more resins having both epoxy and hydroxy functionality can also be used.

Examples of hydroxy-containing resins include, for example, hydroxy functional polyesters, polyethers, polyurethanes, or acrylics, prepared using methods generally known to those skilled in the art.

Epoxy functional resins can include, for example, acrylics having a glycidyl moiety, such as glycidyl methacrylate. The resin used can also be something that is typically regarded as an epoxy crosslinker, such as triglycidyl isocyanurate ("TGIC").

Polyepoxides can also be used as a source of epoxy functionality. The polyepoxides used in the present compositions are those that are suitable for use in powder coatings, such as those that contain at least two 1,2-epoxide groups per molecule. In general, the epoxy equivalent weight can range from about 180 to about 4000 based on solids of the polyepoxide, such as between about 500 and 1000. The polyepoxides may be saturated or unsaturated, and may be aliphatic, alicyclic, aromatic, or heterocyclic. They may contain substituents such as halogens, hydroxyl groups, and ether groups.

Suitable classes of polyepoxides include epoxy ethers obtained by reacting an epihalohydrin such as epichlorohydrin with a polyphenol in the presence of an alkali. Suitable polyphenols include resorcinol, catechol, hydroquinone, bis (4-hydroxyphenyl)-2,2-propane (Bisphenol A), bis(4-hydroxyphenyl)-1,1-isobutane, bis(4-hydroxyphenyl)-1,1-ethane, bis(2-hydroxyphenyl)-methane, 4,4-dihydroxybenzophenone, and 1,5-dihydroxynaphthalene. The diglycidyl ether of Bisphenol A is especially suitable.

Epoxy resins are commercially available from Resolution Performance Products in their EPON line of resins. Particularly suitable are EPON 1001, EPON 1002, and mixtures thereof.

Other suitable polyepoxides include polyglycidyl ethers of polyhydric alcohols. These compounds may be derived from polyhydric alcohols such as ethylene glycol, propylene glycol, butylene glycol, 1,6-hexylene glycol, neopentyl glycol, diethylene glycol, glycerol, trimethylol propane, and pentaerythritol. These compounds may also be derived from polymeric polyols, provided they meet the Tg limitations needed to maintain stability in the composition of the present invention. Some of these compounds may need to be treated to make them sufficient for use in powder coatings. Epoxy functional acrylic polymers can also be used as starting materials, such as glycidal methacrylate (GMA), as can other epoxy functional compounds, such as triglycidal isocyanurate (TGIC).

Examples of other suitable polyepoxides include polyglycidyl esters of polycarboxylic acids. These compounds may be formed by reacting epichlorohydrin or another epoxy material with an aliphatic or aromatic polycarboxylic acid such as succinic acid, adipic acid, azelaic acid, sebacic acid, maleic acid, 2,6-naphthalene dicarboxylic acid, fumaric acid, phthalic acid, tetrahydrophthalic acid, hexahydrophthalic acid, or trimellitic acid. Dimerized unsaturated fatty acids containing about 36 carbon atoms (Dimer Acid) and polymeric polycarboxylic acids such as carboxyl terminated acrylonitrile-butadiene rubber may also be used in the formation of these polyglycidyl esters of polycarboxylic acids.

Polyepoxides derived from the epoxidation of an olefinically unsaturated alicyclic compound are also suitable for use in the curable composition of the present invention. These polyepoxides are nonphenolic and are obtained by epoxidation of alicyclic olefins with, for example, oxygen, perbenzoic acid, acid-aldehyde monoperacetate, or peracetic acid. Such polyepoxides include the epoxy alicyclic ethers and esters well known in the art.

Other suitable polyepoxides include epoxy novolac resins. These resins are obtained by reacting an epihalohydrin with the condensation product of aldehyde and monohydric or polyhydric phenols. A typical example is the reaction product of epichlorohydrin with a phenol-formaldehyde condensate. When the epoxy-containing resin used in the present invention is a polyepoxide, the powder composition cures in the absence of any additional component.

In another embodiment of the present invention, the resin used as component (b) is at least one siloxane-containing resin. As noted above, the term "siloxane-containing resin" refers to any resin that has at least one siloxane moiety and at least one hydroxyl group. These resins are widely commercially available. A suitable selection of siloxane resins is available from Wacker Chemie in its SILRES line of products.

Typically, the resin of component (b) is present in the curable composition of the present invention in a range of from about 20 to about 90 weight percent, such as about 30 to 60 weight percent, based upon the total weight of the curable composition. The material of component (a) is typically present in the compositions of the invention in a range of from about 0.1 to 10 weight percent, such as 0.5 to 5 weight percent. It is expected that the rate of cure increases as the concentration of component (a) increases, and that these increases are directly proportional to each other. It is surprising, however, that no decrease in chemical or mechanical stability is noted as higher catalyst levels are used; stability often behaves inversely proportional to reactivity, in that as reactivity increases, stability decreases. This maintained stability with increased reactivity is yet another advantage of the present invention.

The powder coating compositions of the present invention may optionally contain additives such as waxes for flow and wetting, flow control agents, such as poly(2-ethylhexyl) acrylate, degassing additives such as benzoin and MicroWax C, adjuvant resin to modify and optimize coating properties, antioxidants and the like. These optional additives, when used, can be present in amounts up to 10 weight percent, based on total weight of the coating composition, and if used will typically comprise about 1 to 5 weight percent. Any of various pigments standardly used in the powder coatings art can also be included. Pigment weight can be up to 80 percent of the weight of the entire coating and usually is around 35 weight percent of the coating. The compositions can further comprise a plurality of particles, such as organic or inorganic particles, or mixtures thereof, that contribute to the mar and/or scratch resistance of the coatings. Such particles are described in Ser. No. 10/007,149, filed on Dec. 5, 2001, which is hereby incorporated by reference. Pigments or solid additives in nanoparticulate form can also be included in the present compositions for the same purpose.

It is both a significant and surprising discovery that the present compositions can cure at low temperature in the absence of any additional components, such as a crosslinking agent and/or accelerator typically used in conjunction with epoxy-containing resins and siloxane-containing resins, and thought to be required. For example, siloxanes with active hydrogen groups or alkoxy groups have been previously reported only to cure with compounds that are reactive with these groups such as alkoxylated melamines, urea/formaldehyde crosslinking agents, polyisocyanates and anhydrides. Although the inventors do not wish to be bound by any mechanism, it is believed that the component (a) of the present invention catalyzes the reaction of the epoxide molecules or siloxane molecules with themselves. This is in contrast to the standard mechanism of action, in which such a catalyst would be expected to facilitate the reaction between the functional groups on the resin and a crosslinking agent. Thus, the present invention is further directed to a method for initiating self-cure of an epoxy-containing resin and/or a siloxane-containing resin by adding any of the catalysts described herein to an epoxy-containing resin and/or a siloxane-containing resin.

In the embodiment of the present invention wherein the epoxy-containing resin is an epoxy/hydroxy-containing resin, it is believed that a dual cure mechanism is occurring. More specifically, it is believed that the epoxy and hydroxy functionality cure with each other; it is also believed that component (a) used in the present composition catalyzes the reaction of epoxy groups with themselves. The inventors do not wish to be bound by any mechanism, however.

The crosslink density of the cured coating compositions can be controlled to a large extent by controlling the amount of catalyst added to the composition. Higher amounts of catalyst usually gel the films faster and may crosslink the films more efficiently. Significantly, the present compositions, upon curing, have performance properties at least equal to that of conventional powder coatings in which conventional crosslinkers are used. This refers to the ability to maintain appearance as measured by a number of properties relevant to cured coatings, such as resistance to solvents, pencil hardness, and impact and corrosion resistance. The present compositions also offer additional benefits, such as the cost savings associated with the ability to cure at low temperature. Moreover, the elimination of crosslinkers and/or accelerators in certain embodiments of the present invention is a further cost savings.

The present coating compositions can be prepared by standard methods known in the art. For example, the components are first thoroughly mixed to ensure spatial homogeneity of the ingredients. The composition is then intimately melt kneaded in an extruder. Typical zone temperatures during extrusion range from 40° C. to 125° C., such as 45° C. to 100° C. The exiting extrudate is rapidly cooled to terminate polymerization. The resulting chip is then micronized into powder with an average particle size of 0.1 to 200 microns, such as 1 to 100 microns. Comminution methods are well known. Comminution can be accomplished, for example, by air-classifying mills, impact mills, ball mills, or other fracture-induced mechanisms. Post additives that improve fluidization of the powder mass and/or improve the resistance to impact fusion may be incorporated into the final product before or after micronization. As noted, the use of standard powder coating preparation methods is another advantage of the present invention.

Accordingly, the present invention is further directed to powder coating compositions that cure at a temperature of between 80° C. and 125° C. comprising a resin and curing agent and wherein substantially all of the curing agent is extruded with the resin; "substantially all" means the amount of curing agent needed to completely cure the resin. The present invention is further directed to such compositions that do not cure at temperatures below about 70° C., such as at ambient temperature, like many commercially available low-cure products.

Typically, the present powder coatings will have average particle sizes that range between 15 and 200 microns, such as between about 25 and 50 microns.

The powder coating compositions of the present invention can be applied to a substrate in any number of ways, most often by electrostatic spraying. The powder coating can be applied in a single sweep or in several passes to provide a film having a thickness after cure of from about 1 to 10 mils (25 to 250 microns), usually about 2 to 4 mils (50 to 100 microns). Other standard methods for coating application can also be employed.

After application, the present compositions may be cured by heating to a temperature of between about 80° C. and 190° C., preferably between about 80° C. and 125° C., for a period ranging from about 3 minutes to 30 minutes, such as 10 to 20 minutes. Heating can be effected by any means known in the art, typically by placing the coated substrate in an oven. IR radiation can also be used to heat cure the coated substrates.

Accordingly, the present invention is further directed to methods for coating a substrate comprising applying to the substrate one or more of the coating compositions described herein and curing the coating at a temperature of between about 80° C. and 190° C., such as between about 80° C. and 165° C. or between about 105° C. and 150° C. It is believed that in such methods, the epoxy in the epoxy-containing resin embodiment or the siloxane in the siloxane-containing resin embodiment will self-cure, or react with itself by homopolymerization; this reaction is catalyzed by the present tertiary aminourea or tertiary aminourethane compositions. Accordingly, the present invention is further directed to a cured coating layer comprising an epoxy-containing resin and/or siloxane-containing resin and one or more of the catalysts described herein, wherein the epoxy and/or siloxane have self-cured. For some embodiments, wherein an additional curing agent is used, the resins will undergo both a self-cure and crosslinking with the curing agent.

A number of substrates are suitable for coating according to the methods of the present invention, including plastics such as thermosets or thermoplasts, cardboard, paper, wood, metal, particleboard and medium density fiberboard or mixtures thereof. Substrates coated according to the present methods are also within the scope of the present invention.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa. Also, as used herein, the term "polymer" is meant to refer to oligomers and both homopolymers and copolymers; the prefix "poly" refers to two or more.

EXAMPLES

The following examples are intended to illustrate the invention, and should not be construed as limiting the invention in any way.

Example 1

The following ingredients were used to prepare a catalyst of Formula I, wherein an acidic hydrogen-containing compound is used.

| Ingredient | Weight, g | Equivalents | Percent by weight |
|---|---|---|---|
| Dimethylaminopropylamine | 204.4 | 1.000 | 23.95% |
| Isophorone diisocyanate ("IPDI")[1] | 222.2 | 1.000 | 26.05% |
| Bisphenol A ("BPA")[2] | 426.6 | 3.74 | 50.00% |

[1]Available from Hüls America, Inc.
[2]4,4'-Isopropylidenediphenol, available from Dow Chemical Co.

The dimethylaminopropylamine was charged to a suitable reactor and heated to 50° C. The IPDI was added through an addition funnel over a period of two hours. The temperature of the reaction mixture was allowed to increase to 90° C. during the addition. After the addition was complete the reaction mixture was heated to 130° C. and held at that temperature until infrared analysis indicated consumption of the isocyanate. The reaction mixture was then heated to 160° C. and the Bisphenol A was added. The reaction mixture was held at 160° C. until the solution turned clear, indicating complete melting of the Bisphenol A. The reaction mixture was poured out hot and allowed to cool and solidify. The final solid product had a solids content of about 98 percent and a number average molecular weight of 336 as measured by gel permeation chromatography using polystyrene as a standard.

Example 2

The following ingredients were used to prepare a catalyst of Formula I, wherein an acidic hydrogen-containing compound is not used.

| Ingredient | Weight, g | Equivalents | Percent by weight |
|---|---|---|---|
| Dimethylaminopropylamine | 204.4 | 1.000 | 47.9% |
| Isophorone diisocyanate (IPDI) | 222.2 | 1.000 | 52.1% |

The dimethylaminopropylamine was charged to a suitable reactor and heated to 50° C. The IPDI was added through an addition funnel over a period of two hours. The temperature of the reaction mixture was allowed to increase to 90° C. during the addition. After the addition was complete the reaction mixture was heated to 130° C. and held at that temperature until infrared analysis indicated consumption of the isocyanate. The reaction mixture was poured out hot and allowed to cool and solidify. The final solid product had a solids content of about 98 percent and a number average molecular weight of 336 as measured by gel permeation chromatography using polystyrene as a standard.

Example 3

Samples 1 to 4 were prepared using the components and amounts shown in TABLE 1, including the products prepared according to Examples 1 and 2. The coatings were prepared by premixing the ingredients in a three-blade mixer rotating at 3500 rpm. The premix was then extruded in a 19 mm dual screw extruder operating at a temperature of 80° C. The extrudate was rapidly cooled and pressed into chip. The chip was micronized to an average particle size of 35 microns using a Hosokawa Air-Classifying Mill (ACM).

TABLE 1

| | Sample 1 | Sample 2 | Sample 3 | Sample 4 |
|---|---|---|---|---|
| EPON 1001[3] | — | — | 340 g | 340 g |
| EPON 2002[4] | — | — | 140 g | 140 g |
| DER 642[5] | — | 480 g | — | — |
| PD 9060 (GMA Acrylic)[6] | 480 g | — | — | — |
| Product of Example 1 | 15 g | 15 g | 15 g | — |
| Product of Example 2 | — | — | — | 7.5 g |
| Benzoin[7] | 4 g | 4 g | 4 g | 4 g |
| Modaflow[8] | 9 g | 9 g | 9 g | 9 g |
| Goresil 210[9] | 50 g | 50 g | 50 g | 50 g |
| TiO$_2$ | 150 g | 150 g | 150 g | 150 g |

[3]EPON 1001 is a BPA epoxy having hydroxy functionality, a hydroxy equivalent weight of 389, standard hybrid type, with an epoxy equivalent weight is 550 from Resolution Performance Products.
[4]EPON 2002 is a BPA epoxy, standard hybrid type, with an epoxy equivalent wt = 750, and OH equivalent weight equals 376 from Resolution Performance Products.
[5]DER 642 is a NOVALAC resin from Dow Chemical.
[6]PD 9060 is a GMA Acrylic resin from Anderson Development.
[7]Added as a degasser.
[8]An acrylic copolymer flow additive, anti-crater additive, from Solutia, Inc.
[9]Silica particles, average particle size 2 microns, largest particle size 10 microns, from CED Process Minerals, Inc.

The coatings were sprayed onto Bonderite 1000 steel panels and cured at 115.6° C. for 25 minutes. Following cure, the panels were subjected to a number of tests standard in the industry for testing coatings. Tests and results are shown in TABLE 2.

TABLE 2

|  | Sample 1 | Sample 2 | Sample 3 | Sample 4 |
| --- | --- | --- | --- | --- |
| 100 MEK double rubs[10] | No scuff | No scuff | No scuff | No scuff |
| Impact Reverse/Direct[11] | <20/<20 | 70/100 | 160/160 | 160/160 |
| QUV 340 400 hrs[12] | 60 → 60 | 60 → 20 | 60 → 15 | 60 → 15 |
| Appearance[13] | PCI = 1 | PCI = 7 | PCI = 7 | PCI = 6 |
| Gel time[14] | 6:00 | 3:00 | 3:00 | 3:00 |
| 1000 hrs salt fog 100F.[15] | 2 mm creep | <1 mm creep | <1 mm creep | <1 mm creep |
| 1000 hrs cond hum 100F.[16] | <1 mm creep | <1 mm creep | <1 mm creep | <1 mm creep |
| Powder stability (chemical)[17] | 6:00 | 3:00 | 3:00 | 3:00 |

[10]Powder Coatings Institute ("PCI") #8 Recommended Procedure. ("No scuff" means the coating is fully cured.)
[11]ASTM D2794 (Range <20 to 160 in*lbs.; 160 in*lbs = full flexibility.)
[12]ASTM D4587 (results reported in 20° gloss readings taken initially → after 400 hours of QUV exposure.)
[13]PCI visual standards (Range 1 to 10 - 10 being the smoothest.)
[14]PCI #6 Recommended Procedure (gel time reported in minutes:seconds.)
[15]ASTM B117 (<1 mm = no salt fog effect.)
[16]ASTM D1735 (<1 mm creep = no humidity effect.)
[17]PCI #1 Recommended Procedure at 32° C. (stability reported in minutes:seconds.)

The results in TABLE 2 confirm that a variety of epoxy/hydroxy resins can be cured at low temperature according to the present invention. The acrylic sample (Sample 1) performed as would be expected in the impact and QUV testing—that is, not as well on the former and very well on the latter. Bisphenol A epoxies having hydroxy functionality (Samples 3 and 4) work especially well with the present invention providing the highest level of impact resistance, humidity and salt fog resistance, and chemical resistance; although QUV results were lower than with other samples, this would be expected with this type of resin. One skilled in the art could choose the appropriate resin based on the desired qualities of the cured coating, using the present catalysts to effect cure at low temperatures.

Example 4

Sample 3 prepared as described above was tested for stability using standard techniques as discussed below. The stability of Sample 3 was also compared with the stability of Sample 5, prepared in the same manner as Sample 3 except using three grams of 2-methyl imidazole as the catalyst instead of the catalyst prepared according to Example 1. A standard polyepoxide resin cured with an acid polyester was also compared (PCF 80147, commercially available from PPG Industries, Inc.). The coatings were applied as described in Example 2. However, the commercially available product was cured at a higher temperature (162.8° C.) compared to 115.6° C. for Sample 3 and Sample 5.

TABLE 3

|  | PCF 80147 | Sample 3 | Sample 5 |
| --- | --- | --- | --- |
| Mechanical Stability One week at 32° C. | Excellent | Excellent | Excellent |
| Chemical stability |  |  |  |
| Initial Gel @ 145° C. | 4:00 | 3:00 | 1:30 |
| Gel after One Week @ 32° C. | 4:00 | 3:00 | :40 |
| 100 MEK Double rubs | No Scuff | No Scuff | No Scuff |

The chemical stability and mechanical stability tests were identical, and were performed by placing virgin, free-flowing powder in a sealed jar and setting the jar in a water bath heated (PCI #1 Recommended Procedure, as described in TABLE 2). After one week the samples were evaluated for mechanical stability using a visual ranking. A free-flowing powder is excellent; the ranking standardly used in the industry is as follows:

excellent>good>cakey>clumpy>fused>sintered. All samples had an excellent mechanical stability.

After the visual ranking for mechanical stability, gel times of the aged powder were taken as per PCI #6 Recommended Procedure to assess the chemical stability of the powder coating. A slower gel time translates to advancement in molecular weight. A powder coating should not have molecular weight advancement during storage. As shown in TABLE 3, only Sample 5 (2-methyl imidazole catalyst) showed advancement; the commercial product and the product of the present invention did not advance over time.

Solvent cure (100 MEK double rubs—PCI #8 Recommended Procedure) was used as an indication of film cure. When a film has excellent solvent resistance, that is a good indication that complete cure has occurred. Sample 3 of the present invention underwent complete cure just as the other samples tested.

Thus, the low-cure composition of the present invention performed equal to a commercially available high cure product using conventional crosslinkers and performed better than a sample using a low temperature curing agent outside the scope of the present invention.

Example 5

Sample 6 was prepared by combining the ingredients shown in Table 4 according to Example 3. Sample 6 was coated onto panels and tested, also as described in Example 3.

TABLE 4

|  | Sample 6 |
| --- | --- |
| ALBESTER 3110[18] | 352 g |
| CRYLCOAT 290[19] | 48 g |
| TGIC[20] | 135 g |
| URAFLOW B | 4 g |
| TiO$_2$ | 214 g |
| W-10 BARYTES[21] | 58 g |
| RESIFLOW PL-200 | 8 g |
| Product of Example 1 | 20 g |
| Gel time at 145° C. | 0:55 |
| 100 MEK double rubs | No scuff |

[18]Hydroxyl functional polyester, OH equivalent weight = 190, commercially available from Eastman Chemical Company.
[19]Hydroxyl functional polyester, OH equivalent weight = 1870, commercially available from UCB Chemical.
[20]Triglycidyl isocyanurate-epoxy functional resin, commercially available from Vantico, Inc.
[21]Barium sulfate filler, commercially available from Mountain Minerals.

Sample 6 combines two hydroxy-containing resins with an epoxy resin and the catalyst of the present invention. Again, chemical resistance was excellent. The gel time was again fast at 55 seconds, on a gel plate of 145° C. In addition, the compound cured after a 25 minute bake at 121° C., which is lower than standard epoxy hybrid chemistries.

Example 6

Sample 7 was prepared by combining the ingredients shown in Table 5 according to Example 3. Sample 7 was coated onto panels and tested, also as described in Example 3.

TABLE 5

|  | Sample 7 |
| --- | --- |
| SILRES 604[22] | 500 g |
| URAFLOW B | 3.6 g |
| RESIFLOW PL-200 | 7.3 g |
| Powder mate 542DG[23] | 5 g |
| TiO2 | 200 g |
| Product of Example 1 | 5 g |
| Gel time at 145° C. | 1:05 |
| 100 MEK double rubs | No scuff |

[22]Siloxane resin, commercially available from Wacker-Chemie GMBH.
[23]Degassing agent, commercially available from Micro Powders.

Sample 7 uses a siloxane resin in conjunction with the catalyst of the present invention. Again, chemical resistance was excellent. Gel time was 65 seconds on a 145° C. gel plate with only 1 percent catalyst on resin. In addition, the composition cured after a 25 minute bake at 149° C., yielding a cured film showing no scuff after 100 MEK double rubs.

Whereas particular embodiments of this invention have been described above for purposes of illustration, it will be evident to those skilled in the art the numerous variations of the details of the present invention may be made without departing from the invention as defined in the appended claims.

what is claimed is:

1. A curable powder composition comprising:
(a) at least one material having the structure of Formula I:

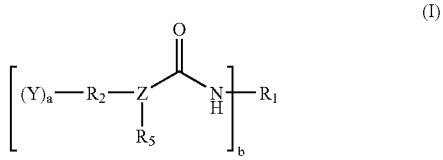

wherein $R_1$, is an organic radical having 6 to 25 carbon atoms; each $R_2$ is independently a multivalent hydrocarbon group having 1 to 20 carbon atoms; Y is

each $R_3$ and $R_4$ are independently alkyl or aryl groups having 1 to 8 carbon atoms; each Z is independently oxygen or nitrogen; $R_5$ is absent when Z is oxygen and $R_5$ is hydrogen, an alkyl or aryl group having 1 to 20 carbon atoms, or $(Y)_a$—$R_2$ — when Z is nitrogen; a is at least 1; b is 1 to 3; and
(b) at least one epoxy-containing resin and/or at least one siloxane-containing resin; and when the epoxy-containing resin is a polyepoxide, Z is nitrogen, $R_2$ is alkylene having 1 to 4 carbons, $R_3$ and $R_4$ are alkyl groups having 1 to 4 carbons, the composition cures in the absence of any additional component.

2. The curable powder composition of claim 1, wherein said composition cures at a temperature of between 80° C. and 125° C.

3. The curable powder composition of claim 2, wherein said composition cures at a temperature of between 105° C. and 120° C.

4. The curable powder composition of claim 1, wherein said composition cures at a temperature greater than 125° C.

5. The curable powder composition of claim 1, wherein Z is nitrogen, and $R_5$ is hydrogen.

6. The curable powder composition of claim 5, wherein $R_1$ is 1,3,3-trimethylcyclohexylmethylene or 1,1,3,3-tetramethylcyclohexylene.

7. The curable powder composition of claim 5, wherein $R_2$ is n-propylene.

8. The curable powder composition of claim 5, wherein $R_3$ and $R_4$ are methyl.

9. The curable powder composition of claim 1, wherein (a) is present in an amount ranging from about 0.5 to 10 weight percent, and (b) is present in an amount ranging from about 20 to about 90 weight percent, with weight percent being based upon total weight of the composition.

10. The curable powder composition of claim 9, wherein (a) is present in an amount ranging from about 3 to 5 weight percent, and (b) is present in an amount ranging from about 30 to about 60 weight percent, with weight percent being based upon total weight of the composition.

11. The curable powder composition of claim 1, wherein the epoxy-containing resin comprises polyepoxide and the powder composition cures in the absence of any additional component.

12. The curable powder composition of claim 1, wherein the resin is a siloxane-containing resin.

13. A cured coating layer comprising:
(a) a material having Formula I:

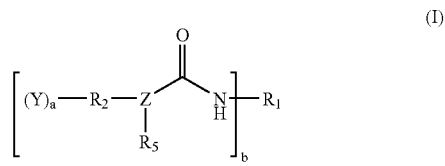

wherein $R_1$ is an organic radical having 6 to 25 carbon atoms; each $R_2$ is independently a multivalent hydrocarbon group having 1 to 20 carbon atoms; Y is

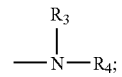

each $R_3$ and $R_4$ are independently alkyl or aryl groups having 1 to 8 carbon atoms; each Z is independently oxygen or nitrogen; $R_5$ is absent when Z is oxygen and $R_5$ is hydrogen, an alkyl or aryl group having 1 to 20 carbon atoms, or $(Y)_a$—$R_2$— when Z is nitrogen; a is at least 1; b is 1 to 3; and
(b) at least one epoxy-containing resin and/or at least one siloxane-containing resin;
wherein the epoxy and/or the siloxane has reacted with itself during cure and said cure takes place in the absence of an additional crosslinker.

14. A method for initiating self-cure of an epoxy-containing resin and/or a siloxane-containing resin comprising adding to a composition comprising said resin(s) a catalyst having the structure:

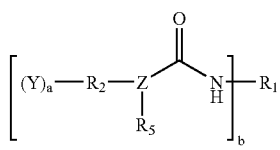

wherein $R_1$ is an organic radical having 6 to 25 carbon atoms; each $R_2$ is independently a multivalent hydrocarbon group having 1 to 20 carbon atoms; Y is

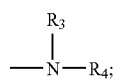

each $R_3$ and $R_4$ are independently alkyl or aryl groups having 1 to 8 carbon atoms; each Z is independently oxygen or nitrogen; $R_5$ is absent when Z is oxygen and $R_5$ is hydrogen, an alkyl or aryl group having 1 to 20 carbon atoms, or (Y)a —$R_2$— when Z is nitrogen; a is at least 1; b is 1 to 3.

15. The curable powder composition of claim 1, wherein $R_2$ is alkylene.

16. The curable powder composition of claim 1, wherein $R_3$ and $R_4$ are alkyl.

* * * * *